United States Patent [19]
Lamprecht

[11] Patent Number: 5,782,926
[45] Date of Patent: Jul. 21, 1998

[54] WRIST PROSTHESIS

[75] Inventor: Stefan Lamprecht, Birchwil, Switzerland

[73] Assignee: Sulzer Orthopaedie AG, Baar, Switzerland

[21] Appl. No.: 666,982

[22] Filed: Jun. 20, 1996

[30] Foreign Application Priority Data

Jun. 21, 1995 [EP] European Pat. Off. ............ 95810419

[51] Int. Cl.$^6$ ..................................................... A61F 2/42
[52] U.S. Cl. ........................................................... 623/21
[58] Field of Search ................................................. 623/21

[56] References Cited

FOREIGN PATENT DOCUMENTS 0 607 749   7/1994   European Pat. Off. .
2 269 752   2/1994   United Kingdom .

*Primary Examiner*—John G. Weiss
*Assistant Examiner*—John M. Black
*Attorney, Agent, or Firm*—Townsend and Townsend and Crew LLP

[57] ABSTRACT

The artificial hand joint comprises a proximal joint part securable to the radius with a groove-like guide track and a distal joint part securable to the os capitatum with two supporting heads placed alongside one another, displaceable in the guide track in the direction of their longitudinal extent, and mounted so as to be inclinable in the transverse direction. These are executed with spherical support parts, each of which cooperates with a guidance section of the guide track. By means of the two supporting heads a stable guidance of the distal joint part in the direction of the extension movements is achieved. The guide track and the proximal joint part can be executed with advantageously small cross sectional dimensions so that the intrusions into the implantation region of the hand joint can be kept to a minimum.

9 Claims, 1 Drawing Sheet

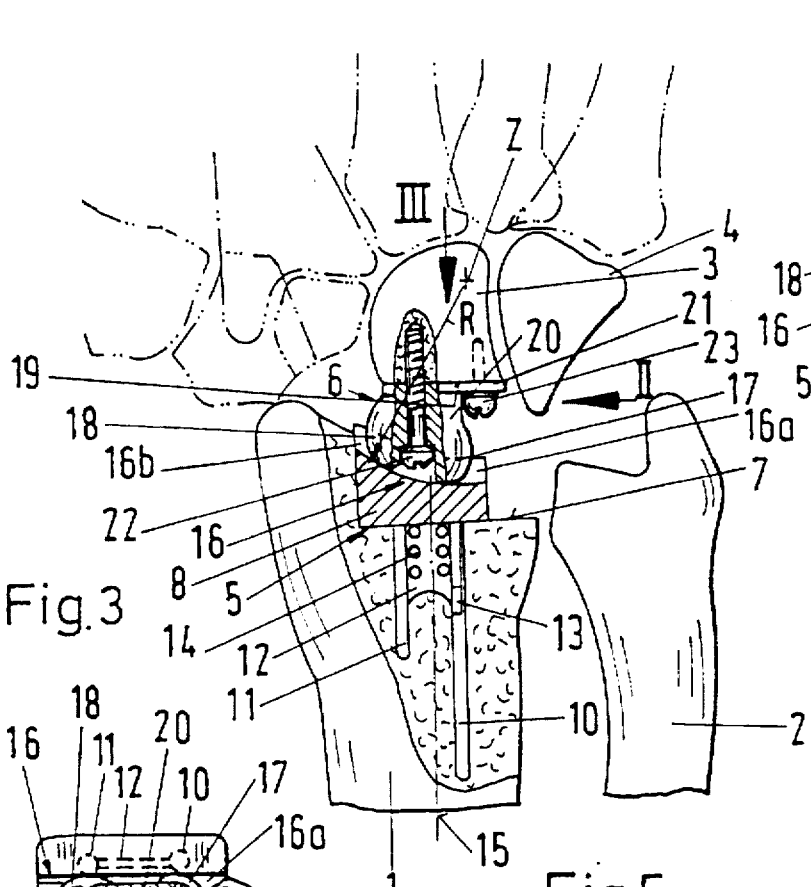
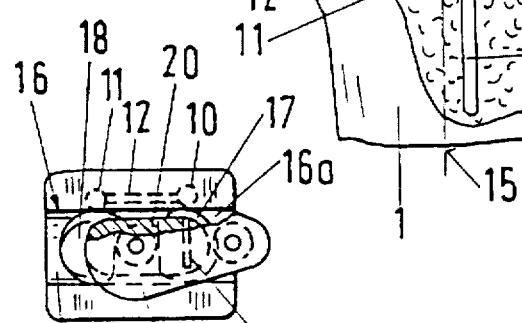
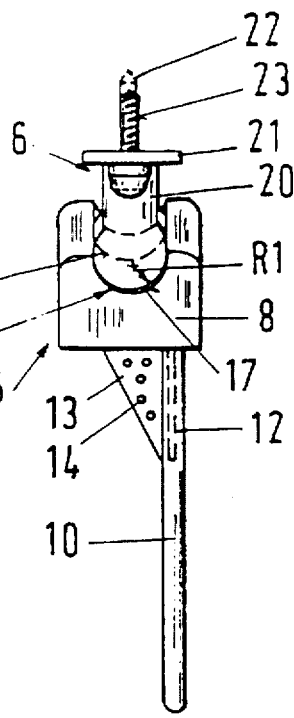
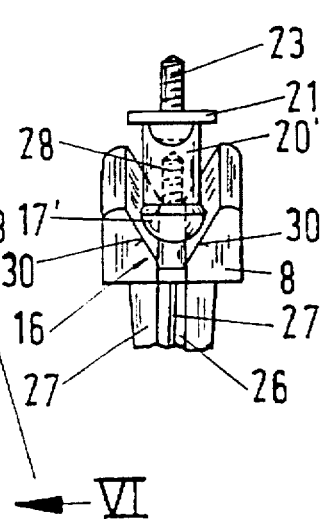
Fig.1
Fig.2
Fig.3
Fig.4
Fig.5
Fig.6

WRIST PROSTHESIS

BACKGROUND OF THE INVENTION

1. Technical Field of the Invention

The invention relates to an artificial hand joint, and more particularly to a wrist prosthesis for executing flexion and extension of a hand.

2. Description of the Prior Art

An artificial hand joint is known from EP-A-0 607 749 and contains a distal spherical supporting head and a proximal counterpiece with a groove-like guide track for the supporting head. The known embodiment permits flexion and extension movements, where the range of the extension movements is determined in the individual case by two raised end portions of the guide track limiting the longitudinal displacements of the supporting head. Within the so-limited range of movement, however, the supporting head is unguided in the direction of the extension movements so that it can perform lateral tilting movements in the longitudinal direction of the guide track. Thus the hand part connected with the supporting head can adopt laterally unguided indeterminate angular positions with respect to the longitudinal axis of the radius, which are limited only by the ligaments and tendons of the hand part. The supporting head and the counterpart of the known joint arrangement are furthermore each executed with a central pin which is to be anchored in the corresponding bone and is provided with longitudinal ribs. Each of these pins requires a relatively voluminous execution and hence correspondingly large excavations to be machined into the bones for the reception of these anchoring parts, thus weakening their cross sections. In order to ensure unimpeded flexion and extension movements of the co-operating parts of the hand joint for the known joint arrangement, the supporting head and guide track must each be executed with a relatively large supporting surface, which requires a correspondingly broad execution of the counterpart in the direction of the flexion movement and thus the creation of a correspondingly large implantation region at the radius.

SUMMARY OF THE INVENTION

The object of the present invention is to provide a further developed and improved implant of the initially named type in a compact design, which enables a secure emplacement of the co-operating parts in the implantation region with as little loss of bone matter as possible, and which permits unimpeded flexion and extension movements of the co-operating parts as well as an improved guidance of the distal joint part within its range of movement running in the direction of the extension movement.

This object is satisfied in accordance with the invention by a wrist prosthesis for executing flexion and extension of a hand, the prosthesis comprising a proximal joint part and a distal joint part. The distal joint part is configured to be secured to the capitate bone and has a first supporting head with a first crowned supporting surface and a second supporting head with a second crowned supporting surface adjacent the first supporting head along the direction of extension. The proximal joint part is configured to be secured to the radius and has a groove-shaped guide track having first and second sections oriented perpendicular to a longitudinal axis of the radius for receipt of each of the first and second supporting heads, respectively, thereby allowing unimpeded extension movement while maintaining lateral stability of the distal joint part throughout the extension movement.

The hand joint executed in accordance with the present invention enables unimpeded flexion and extension movements, where the two supporting heads ensure a lateral stability of the distal joint part during the extension movements and thus a defined angular position of the distal hand region in every case with respect to the lateral axis of the radius. The supporting surfaces of the two supporting heads can each be executed with a relatively small radius of curvature, so that the guide track as well as the guide piece receiving the supporting heads can be executed with a correspondingly small width, and hence the implantation region to be produced by removal of bone matter can be kept small and the intrusion into the bone region of the hand joint kept to a minimum. A further advantage of the embodiment in accordance with the invention consists of the fact that the implants can each be manufactured in a light-weight construction of small dimensions, which nevertheless ensure a secure anchoring of the joint parts in the bones of the hand region.

BRIEF DESCRIPTION OF THE DRAWINGS

FIG. 1 is a plan view of an installed hand joint in accordance with the present invention in a plane determined by the radius and the ulna, with joint parts in a partial section, FIGS. 2 and 3 are enlarged elevational views of the joint parts in a larger representation and seen in accordance with arrows II—II or III—III in FIG. 1, respectively, FIG. 4 is an elevation view of corresponding joint parts of a hand joint in accordance with an alternative embodiment seen in accordance with arrow II—II in FIG. 1, FIG. 5 is a partial plan view of a hand joint in accordance with another alternative embodiment with joint parts in partial section, and FIG. 6 is a side elevation view of the joint parts seen in accordance with arrow VI in FIG. 5.

DETAILED DESCRIPTION OF THE PREFERRED EXEMPLARY EMBODIMENTS

FIG. 1 illustrates a hand region contiguous with two forearm bones—radius 1 and ulna 2—in which two distal carpal bones—the os capitatum 3 and the Os hamatum 4—are represented with solid lines and further, unmodified hand bones are represented with chain dotted lines and in which the proximal carpal bones have been removed. The artificial hand joint comprises a proximal joint part 5 securable to the radius 1 and a distal joint part 6 securable to the os capitatum 3. The proximal joint part 5 contains a guide piece 8 which can be placed on a resection surface 7 of the radius 1 with two securing elements projecting therefrom in the form of pins 10 and 11, each anchorable in a corresponding bore in the radius 1, which are united with one another by ribs 12 and 13 which can be inserted into the bone and connected to the guide piece 8 in a manner which is stiff in bending. The ribs 12 and 13 can be provided, as shown in the figure, with passage openings 14 which permit the ingrowth of bone matter and thus, with as little intrusion as possible into the bone region, ensure a secure anchorage of the securing elements in the radius 1. The guide piece 8 is executed with a groove-like guide track 16 running transversely to a longitudinal axis 15 of the radius 1 and orientable in the direction of an extension movement of the hand joint, in which the distal joint part 6 is guided displaceably in accordance with a plane determined by the radius 1 and the ulna 2. The guide track 16 is executed in the form of a groove with a semicircular cross section and a base surface running in an arch over its longitudinal extent, which, as shown in the diagram, is determined by a radius of curvature R whose imaginary center of rotation Z can lie in the region of the Os capitatum 3 after the implantation of the joint parts 5 and 6.

The distal joint part 6 is executed with two supporting heads 17 and 18 arranged at a distance to one another in the direction of the extension movement and insertable into the guide track 16, which are connected via a common neck part 20 to a supporting plate 21 which can be placed onto a resection surface 19 of the os capitatum 3 and is securable to the os capitatum 3 by means of screws 22, 23. As indicated in the diagram the supporting heads 17 and 18 are executed in the form of extensions with spherical supporting surfaces formed on the neck part 20 and thickened with respect to this neck part 20, which each co-operate by in-line contact with a corresponding section 16a or 16b of the guide track 16. The cross section of the guide track 16 is executed with a radius R1 which is larger than the radii of the supporting surfaces of the supporting heads 17 and 18 by a clearance which permits a sliding contact.

The joint parts 5 and 6 can each be formed in several parts or, as shown, as single piece components. A stock of some embodiments can, for example, be kept available which are matched with respect to one another and have dimensions of various sizes. After implantation of the joint parts 5 and 6, if these are held in the anatomically correct position by ligaments and tendons of the ligamentous apparatus not shown, a stable guidance of the co-operating joint parts 5 and 6 in the direction of the extension movement is achieved by the two supporting heads 17 and 18 by the fact that each of the two supporting heads 17 and 18 is displaceably braced on the corresponding section 16a or 16b of the guide track 16, respectively. At the same time, the mobility of the two supporting heads 17 and 18 in the direction of the flexion movements is ensured since the semicircular cross section of the guide track 16, in conjunction with the neck part 20 that is contracted with respect to the supporting heads 17, 18, allows a relatively large swivel movement of the distal joint part 6 transversely to the elongated extent of the guide track 16.

Corresponding to the representation in FIG. 4, the guide track 16 can be bounded by side flanks 25 arranged in a V-form which, when seen in cross section, are each executed with a radius of curvature R2 which is greater than the radii of curvature of the spherical supporting surfaces formed on the supporting heads 17 and 18. Each of the two supporting heads 17 and 18 are correspondingly braced on the flanks 25 of the guide track 16 via two essentially punctiform bracing parts, whereby a stable guidance of the co-operating joint parts 5 and 6 can likewise be obtained in the direction of the extension movement. At the same time the mobility of the supporting heads 17 and 18 perpendicular to the longitudinal extension of the guide track 16 is ensured, since this guide track can be executed with a relatively large breadth and depth, whereby a correspondingly greater swivel range of the co-operating joint parts 5 and 6 can be achieved in the direction of the flexion movements. As is further evident from FIG. 4, the guide piece 8 can also be executed with a central pin 26 which is anchorable in the radius 1 and can be provided with several guidance-ribs 27 (the embodiment illustrated in FIG. 4 has four, for example), radially projecting therefrom and insertable into corresponding slits of the bone part.

According to FIG. 5 the distal joint part 6 can be executed with a holder 20' securable to the os capitatum 3 and with two supporting heads 17' and 18' each individually attachable to this support which, as shown in the figure, are each formed of a hemispherical screw head of a screw 28 anchorable in the holder 20' or of a screw 22' anchorable on the os capitatum 3 passing through the holder 20'. As also seen in FIG. 5 the supporting heads 17' and 18' can be executed with different dimensions and be arranged with correspondingly different penetration depths in the guide track 16. By suitable choice of the supporting heads 17' and 18' the angular setting of the holder 20' can be influenced with respect to the guide track 16 and thus adapted to the individual circumstances in the attaching region of the os capitatum 3.

In accordance with FIG. 6 the guide track 16 of the guide piece 8 can also be bounded by two side flanks 30 converging to its arcuate base area, each of which is executed in the form of a jacket surface of a truncated cone. In accordance with a modified embodiment of the distal joint part 6 not shown, it is possible to execute only one of the supporting heads 17' or 18' as a supporting part securable to the holder 20' and the other supporting head 18' or 17', respectively, as an extension formed on the holder 20'.

In summary the invention may be described as follows:

The artificial hand joint comprises a proximal joint part securable to the radius with a groove-like guide track and a distal joint part securable to the os capitatum with two supporting heads placed alongside one another, displaceable in the guide track in the direction of their longitudinal extent, and mounted so as to be inclinable in the transverse direction. These are executed with spherical support parts, each of which co-operates with a guidance section of the guide track. By means of the two supporting heads, a stable guidance of the distal joint part in the direction of the extension movements is achieved. The guide track and the proximal joint part can be executed with advantageously small cross sectional dimensions so that the intrusions into the implantation region of the hand joint can be kept to a minimum.

What is claimed is:

1. A wrist prosthesis for executing flexion and extension of a hand comprising a proximal joint part and a distal joint part, said distal joint part configured to be secured to the capitate bone and having a first supporting head with a first crowned supporting surface and a second supporting head with a second crowned supporting surface adjacent said first supporting head along the direction of extension; said proximal joint part configured to be secured to the radius and having a groove-shaped guide track having first and second sections oriented perpendicular to a longitudinal axis of the radius for receipt of each of said first and second supporting heads, respectively, thereby allowing unimpeded extension movement while maintaining lateral stability of the distal joint part throughout the extension movement.

2. The wrist prosthesis in accordance with claim 1, wherein the distal joint part has a neck section anchorable by a fastening means to the capitate bone; and wherein said two supporting heads are each formed of an at least partly spherical protrusion projecting from the neck section.

3. The wrist prosthesis in accordance with claim 2 wherein the two supporting heads are each formed at a respective extension formed on the neck section.

4. The wrist prosthesis in accordance with claim 1 wherein at least one of the two supporting heads is formed by a supporting element, said supporting element being securable to the capitate bone.

5. The wrist prosthesis in accordance with claim 1 wherein the guideway of the proximal joint part is executed, when viewed in cross section, with curved guidance surfaces corresponding to supporting surfaces of the supporting heads.

6. The wrist prosthesis in accordance with claim 1 wherein the guideway of the proximal joint part is executed, when viewed in cross section, with guidance surfaces arranged essentially in a V-formation to cooperate with contact parts that are essentially in a form of points of supporting surfaces of the supporting heads.

7. The wrist prosthesis in accordance with claim 1 wherein the proximal joint part is provided with at least two pin-like securing elements arranged side by side in the radius.

8. The wrist prosthesis in accordance with claim 1 wherein at least one of the two supporting heads is formed by a supporting element, said supporting element being securable to the neck section.

9. The wrist prosthesis in accordance with claim 8 wherein the supporting element is also securable to the capitate bone.

* * * * *